(12) United States Patent
Penkler (10) Patent No.: US 7,202,233 B2
(45) Date of Patent: Apr. 10, 2007

(54) ALPRAZOLAM INCLUSION COMPLEXES AND PHARMACEUTICAL COMPOSITIONS THEREOF

(75) Inventor: Lawrence John Penkler, Port Elizabeth (ZA)

(73) Assignee: Farmarc Nederland BV, Amsterdam (NL)

( * ) Notice: Subject to any disclaimer, the term of this patent is extended or adjusted under 35 U.S.C. 154(b) by 0 days.

(21) Appl. No.: 11/144,965

(22) Filed: Jun. 3, 2005

(65) Prior Publication Data

US 2005/0222086 A1    Oct. 6, 2005

Related U.S. Application Data

(63) Continuation-in-part of application No. 10/220,563, filed as application No. PCT/IB01/00321 on Mar. 8, 2001, now abandoned.

(30) Foreign Application Priority Data

Mar. 28, 2000    (ZA) .................... 2000/1567

(51) Int. Cl.
*A61K 31/724* (2006.01)
*A61K 31/517* (2006.01)

(52) U.S. Cl. .................. 514/58; 514/788; 514/252.17; 536/103; 424/488; 424/449; 564/161; 564/229; 544/370

(58) Field of Classification Search ........... 514/58, 514/788, 252.17; 536/103; 564/161, 229; 544/370; 424/488, 449
See application file for complete search history.

(56) References Cited

U.S. PATENT DOCUMENTS 5,472,954 A * 12/1995 Loftsson ............ 514/58

FOREIGN PATENT DOCUMENTS

| WO | WO 99/42111 | * 8/1999 |
|---|---|---|
| WO | WO 00/59475 | 10/2000 |
| WO | WO 02/060411 | 8/2002 |

OTHER PUBLICATIONS

J.M. Scavone et al.; Alpracolam Kinetics Following Sublingual and Oral Administration; Journal; J. Clin. Pyschopharmacol; 1987, 7:332-334; Boston, MA.

Roderick B. Walker and Eric W. Smith; The Role of Percutaneous Penetration Enhancers; Journal; Advanced Drug Delivery Reviews; 18 1996 295-301.

Josef Szejtli: Cyclodextrin Technology; Kluer Academic Press; 1988; Journal; 79, 80-185.

J. Szejtli * K-H Fromming; Cyclodextrins in Pharmacy, Kluwer Academic Press; 19-32, 1988.

Loftsson et al; Improved Acitretin Delivery Through Hairless Mouse Skin by Cyclodextrin Complexation; International Journal of Pharmaceuticals 115; 1995, 255-258.

(Continued)

*Primary Examiner*—Shaojia Anna Jiang
*Assistant Examiner*—Devesh Khare
(74) *Attorney, Agent, or Firm*—Timothy J. Keefer; Seyfarth Shaw LLP (57) ABSTRACT

A pharmaceutical composition an inclusion complex and methods for treating patients and preparing said complex disclosed for transmucosal delivery comprising an inclusion complex of (a) alprazolam and (b) a water soluble 2-hydroxypropyl-beta-cyclodextrin, and a pharmaceutically acceptable carrier therefor, wherein all the alprazolam is present in ring-closed form.

14 Claims, 3 Drawing Sheets

OTHER PUBLICATIONS

Volmer et al.; A study of Percutaneous Absorption-Enhancing Effects of Cyclodextrin Derivative in Rats; Journal; J. Pharm. 1994; 19-22.

Vollmer et al.; In Vivo Skin Pharmaceuticals of Liarozole; Percutaneous Absorbtion Studies with Different Formulations of Cyclodextrin Derivatives in Rats; International Jounal of Pharmaceutics 99 1993 51-58.

Legendre et al; Effects of B-Cyclodextrins on Skin: Implications for the Transdermal Delivery of Piribedil and a Novel Cognition Enhancing-Drug S-9977; Pharmaceutical Sciences European Jounal of Pharmaceutical Sciences 3 1995 311-322.

Merkus et al.; Absorbtion Enhancing Effect of Cyclodextrins on Intranasally Administered Insulin in Rats; Pharmaceutical Research, vol. 8 No. 5 1991 pp. 588-592.

Gill et al.; Cyclodextrins as Protection Agents Against Enhancer Damage in Nassal Delivery Systems I. Assessment of Effect by Measurement of Erythrocyte Haemolysis; Pharmaceutical Sciences; European Journal of Pharmaceutical Sciences 1 1994 229-236.

Stella et al. The Interaction of Charged and Uncharged Drugs with Neutral and Anionically Charged Cyclodextrin; Pharmaceutical Research 1995, 12 9 S205.

Bergeron et al.; Disposition Requirements for Binding in Aqueous Solution of Polar Substrates in the Cyclohexaamylose Cavity; Journal of the American Chemical Society 99:15; Jul. 20, 1977.

Loftsson et al.; Solubilization and Stabilization of Drugs Through Cyclodextrin Complexation; Acta Pharm. Nord 3(4) pp. 215-217; 1991.

Loftssib et ak.; The effect of Water Soluble Polymers on Drug-Cyclodextrin Complexation; International Journal of Pharmaceutics; 110; 1994 pp. 169-177.

Loftsson et al.; The Effect of Water Soluble Polymers on the Aqueous Solubility and Complexing Abilities of B-Cyclodextrin; International Journal of Pharmaceuticals 163; 1998 pp. 115-121.

* cited by examiner

HPLC Chromatogram - Alprazolam Ring Open and Ring Closed

ALPRAZOLAM INCLUSION COMPLEXES AND PHARMACEUTICAL COMPOSITIONS THEREOF

CROSS REFERENCE TO RELATED APPLICATION

This application is a Continuation in Part of U.S. patent application Ser. No. 10/220,563, entitled "ALPRAZOLAM INCLUSION COMPLEXES AND PHARMACEUTICAL COMPOSITIONS THEREOF, filed Oct. 30, 2002 now abandoned which claims priority of International Patent Application No. PCT/IB01/00321, filed Mar. 8, 2001 and South African application 2000/1567 filed Mar. 28, 2000.

BACKGROUND OF THE INVENTION

This invention relates to an inclusion complex of alprazolam and 2-hydroxypropyl-beta-cyclodextrin, and to pharmaceutical compositions containing such a complex, particularly for oral, nasal or rectal mucosal delivery, for the treatment of anxiety and panic attack.

Alprazolam is also known as 8-chloro-1-methyl-6-phenyl-4H-[1,2,4]triazolo[4,3a][1,4]benzodiazepine.

Alprazolam is indicated for the short term treatment of Generalised Anxiety Disorder (GAD) and has particular utility as an agent for the management of panic disorders (with or without agoraphobia).

In an acute state such as a panic attack, a rapid onset of action is desirable. Although alprazolam is well absorbed from a tablet formulation after conventional orogastric administration, maximum plasma levels occur between 0.7 to 1.8 hours post-dose. The onset of anxiolysis correlates with attainment of maximum plasma levels. The absorption rate is therefore often not sufficiently rapid to provide immediate symptomatic relief in an anxiety crisis.

Absorption of alprazolam from the stomach is further adversely affected by the presence of food and antacids, the use of the latter being frequently associated with stress related syndromes. Rapid absorption of alprazolam in a manner which would avoid these complications and avoid the need for administration of the dosage form with a liquid would have distinct advantages.

The mucosal route of drug delivery, in particular the sublingual or nasal mucosal routes, offer a useful alternative to parenteral delivery where a rapid therapeutic effect is desired. Sublingual use of the commercially available oral tablet dosage forms of alprazolam offers no significant benefit over conventional orogastric administration in terms of speed of onset [see J. M. Scavone etal, J. Clin. Psychopharmacol., 1987, 7, 332–335]. Formulation of alprazolam in a manner which permits rapid uptake from the sublingual, nasal or rectal mucosa would have distinct utility in the emergency relief of anxiety symptoms.

The oral, nasal and rectal cavities have several advantages as sites for systemic drug delivery, particularly avoidance of pre-systemic metabolism.

However, the low permeability of the membranes that line the oral and nasal cavities result in a low flux of drug. There is therefore a need to enhance drug solubility and penetration to improve bioavailability following oral or nasal mucosal drug delivery.

There are several methods known in the art to deliver drugs to the oral, nasal and rectal mucosae. These include buccal and sublingual tablets or lozenges, adhesive patches, gels, solutions or sprays (powder, liquid or aerosol) for the oral cavity and solutions or sprays (powder, liquid or aerosol) for the nasal cavity and suppositories for rectal administration.

The absorption of drugs from mucosal membranes may be enhanced by (i) increasing drug solubility, (ii) pH modification to favour the unionised form of the drug, (iii) addition of mucoadhesive agents to improve contact between the delivery system and the membrane and (iv) incorporation of so-called penetration enhancers.

There are a number of penetration enhancers known to influence the permeability of drugs across epithelial membranes (for a recent review see Walker, R. B. and Smith, E. W. Advanced Drug Delivery Reviews 1996, 18, 295–301).

Cyclodextrins and their derivatives have found extensive application as solubilizers and stabilizers due to their ability to form inclusion complexes with a wide variety of compounds (see J. Szejtli, Cyclodextrin Technology, Kluwer Academic Press) and (J. Szejtli & K-H Fromming, Cyclodextrins in Pharmacy, Kluwer Academic Press).

Cyclodextrins have been used to enhance intestinal absorption of drugs primarily through increasing solubility. Recently, cyclodextrins have been shown to have positive and negative effects on transdermal penetration of drugs (see Loftsson, T. et al. International Journal of Pharmaceutics 1995, 115, 255–258), (Vollmer, U. et al. International Journal of Pharmaceutics 1993, 99, 51–58), (Legendre, J. Y. et al. European Journal of Pharmaceutics 1995, 3, 311–322) and (Vollmer, U. et al Journal of Pharmacy and Pharmacology 1994, 46, 19–22). Cyclodextrins may improve nasal absorption of drugs (see Merkus, F. W. et al. Pharmaceutical Research 1992, 9, 1157–1163) and enhance absorption from sublingual administration of drug/cyclodextrin complexes. Cyclodextrins also protect nasal mucosal damage by penetration enhancers (see Jabbal. Gill, I. et al. European Journal of Pharmaceutical Sciences 1994, 1 (5), 229–236).

Cyclodextrins are water soluble cone-shaped cyclic oligosaccharides containing 6, 7 or 8 glucopyranose units. The interior "cavity" of the cone is hydrophobic whilst the exterior is hydrophilic. The size of the cavity increases with increasing number of glucose units. Several cyclodextrin derivatives such as alkyl, hydroxyalkyl and sulfoalkyl ethers have been prepared with improved solubility (see J. Szejtli & K-H Fromming, Cyclodextrins in Pharmacy, Kluwer Academic Press) and (Stella, V. J. et al. Pharmaceutical Research 1995, 12 (9) S205). Suitably sized hydrophobic "guest" molecules may enter the "host" cavity to form a classical host-guest "inclusion compound" or "inclusion complex" with either the entire guest molecule included or only a portion thereof. The driving mechanism for cyclodextrin inclusion complexation is the affinity of the hydrophobic guest molecule for the cavity of the cyclodextrin host molecule with displacement of cavity water molecules to a thermodynamically more stable state. The term "complex stability" or stability of a given inclusion complex refers to the association/dissociation equilibrium of host and guest in solution. Complex stability depends on the number of intermolecular bonding interactions between the host and guest. Van der Waals forces and hydrophobic interactions are the main interactions stabilising inclusion complexes (Bergeron, R. J. et al. Journal of the American Chemical Society 1977, 99, 5146). Depending on the nature and position of hydrogen bonding functionalities on a given guest, there may be hydrogen bonding between the guest and hydroxyl groups of the cyclodextrin or other hydrogen bonding groups in the case of cyclodextrin derivatives. Ionic interactions between the host and guest are also possible in the case of ionic cyclodextrins such as sulfobutyl ethers (Stella, V. J. et al. Pharmaceutical Research 1995, 12 (9), S205).

Cyclodextrin inclusion complexes may be prepared on the basis of liquid state, solid state or semi-solid state reaction between the components (J. Szejtli, Cyclodextrin Technology, Kluwer Academic Press). The first is accomplished by dissolving the cyclodextrin and guest in a suitable solvent or mixture of solvents and subsequently isolating the solid state complex by crystallisation, evaporation, spray drying or freeze drying. In the solid state method, the two components may be screened to uniform particle size and thoroughly mixed whereafter they are ground in a high energy mill with optional heating, screened and homogenised. In the semi-solid state, the two components are kneaded in the presence of small amounts of a suitable solvent, and the complex so-formed, is dried, screened and homogenised.

The liquid state reaction generally provides optimum conditions for completeness of reaction. Depending on solvent conditions, the dissolved inclusion complex exists in equilibrium between uncomplexed host and guest and complexed host/guest.

The use of cyclodextrins to increase the solubility of alprazolam has been described. In an article in Acta Pharm. Nord. 3 (4), 1991, 215–217, Loftsson et al describe the effect of the cyclodextrin derivative, 2-hydroxypropyl-beta-cyclodextrin, on the aqueous solubility of 13 different drugs, including alprazolam. A 16-fold solubility enhancement for alprazolam in a 20% solution of 2-hydroxypropyl-beta-cyclodextrin is reported. No solid complex is described.

In a subsequent article published in Int. J. Pharm, 1994, 110, 169–177, Loftsson et al describe the effect of 2-hydroxypropyl-beta-cyclodextrin on the water solubility of alprazolam in the presence and absence of water soluble polymers. Enhanced solubility of alprazolam is obtained following heating of a solution of 2-hydroxypropyl-beta-cyclodextrin and a water soluble polymer in a sealed container at 120° C. for 20 minutes. No solid complex is described.

JP 07165616 to Hisamitsu Pharmaceutical Company, Japan similarly claims the formation of inclusion complexes of drugs with cyclodextrin in the presence of water soluble polymers to improve solubility and stability.

Loftsson et al [see Int. J. Pharm, 1998, 162 (2), 115–121] have also reported an enhancement in the solubility and have demonstrated improved complexing ability for beta-cyclodextrin in solutions of drugs containing water soluble polymers, including the drug alprazolam. No solid complex is described.

DE 44 28 986 A1 to KRKA, Slovenia teaches the formulation of rapidly dissolving solid dosage forms for orogastric administration of alprazolam containing alpha-, beta-, or gamma cyclodextrin when employed as water soluble carriers. Alprazolam is deposited on the carrier by spray drying prior to incorporation into a tablet.

U.S. Pat. Nos. 5,288,497 and 5,785,989 to Stanley, T. H. et al (The University of Utah) entitled "Compositions of Oral Dissolvable Medicaments" and "Compositions and Methods of Manufacturing of Oral Dissolvable Medicaments", respectively, recite in their claims a drug-containing dosage form (where the drug is a benzodiazepine) which permits absorption through the mucosal tissues of the mouth. The dosage form is referred to as an "appliance or holder" containing drug dispersed into a carbohydrate, fat, protein, wax or other dissolvable matrix.

In WO 99/42111, Loftsson et al. discuss methods for enhancing cyclodextrin complexation. Loftsson et al deemed it necessary to increase the aqueous solubility and complexation efficiency of the alprazolam by lowering the pH to below 5 in order to formulate alprazolam as a successful formulation for transmucosal delivery. A first drawback of such a formulation with a pH of lower than 5 for transmucosal delivery of an active ingredient is that the lower pH may result in mucosal irritation causing increased saliva production, adversely affecting oral transmucosal drug delivery, thereby decreasing the patient's compliance due to oral mucosal irritation. A formulation causing oral mucosal irritation will increase saliva production, decreasing the efficacy of the sublingual formulation, due to increased swallowing of the alprazolam-cyclodextrin complex. A second drawback is that, in use, the presence of alprazolam ring-open form will in fact negatively influence transport across mucosal membranes since it is well established that absorption of drugs across mucosal membranes is enhanced by favouring the unionised (or ring-closed) form (Rathbone, et al. 1996. Systemic oral mucosal drug delivery and delivery systems, In. Oral mucosal drug delivery, Marcel Dekker:New York, p. 253).

SUMMARY OF THE INVENTION

According to a first aspect of the invention there is provided a pharmaceutical composition for transmucosal delivery comprising an inclusion complex of (a) alprazolam and (b) a water soluble 2-hydroxypropyl-beta-cyclodextrin, and a pharmaceutical acceptable carrier therefor, wherein all the alprazolam is present in ring-closed form.

Preferably, the composition, when in liquid form has a pH greater than 6, and when in solid form has a pH of greater than 6 when reconstituted with water having a pH of 7.

The pharmaceutical acceptable carrier must be suitable for transmucosal delivery of the alprazolam inclusion complex.

The inclusion complex preferably has a stoichiometry of (a) to (b) from 1:1 mol/mol to 1:10 mol/mol inclusive and more preferably 1:7 mol/mol inclusive.

According to a second aspect of the invention there is provided an inclusion complex of (a) alprazolam and (b) a water soluble 2-hydoxypropyl-beta-cyclodextrin, wherein all the alprazolam is in ring-closed form.

The pharmaceutical composition is preferably for use in the treatment of Generalised Anxiety Disorder (GAD) and has particular utility as an agent for the management of panic disorders.

The pharmaceutical composition is preferably adapted for oral, nasal or rectal mucosal delivery.

A third aspect of the invention relates to a method of preparing an inclusion complex of (a) alprazolam and (b) a water soluble 2-hydoxypropyl-beta-cyclodextrin in an aqueous solution wherein all the alprazolam is present in the ring-closed form, wherein the alprazolam and cyclodextrin are added to said solution having a pH of greater than 6, to form said inclusion complex.

Typically, the alprazolam and cyclodextrin have a stoichiometry of from 1:1 mol/mol to 1:10 mol/mol inclusive, preferably the alprazolam and cyclodextrin have a stoichiometry of from 1:1 mol/mol to 1:7 mol/mol inclusive.

Preferably, the 2-hydroxypropyl-beta-cyclodextrin has a degree of substitution between 3.9 and 5.1 hydroxypropyl groups per cyclodextrin molecule.

After the alprazolam and cyclodextrin are added to the water, the pH of the solution may be adjusted to 7.

The inclusion complex may be dried, for example by vacuum or freeze-drying, to provide a solid which, when reconstituted with water having a pH of 7, forms a solution having a pH of greater than 6.

DESCRIPTION OF EMBODIMENTS

The crux of the invention is an inclusion complex of (a) alprazolam and (b) a 2-hydroxypropyl-beta-cyclodextrin, and pharmaceutical compositions containing the inclusion complex for transmucosal delivery, wherein all the alprazolam is present in ring-closed form.

The degree of substitution of the 2-hydroxypropyl-beta-cyclodextrin may vary between 1 to 20 substituents per cyclodextrin molecule, but more preferably between 3 to 15 substituents per cyclodextrin molecule.

The preferred degree of substitution of the 2-hydroxypropyl-beta-cyclodextrin is between 3.9 and 5.1 hydroxypropyl groups per cyclodextrin molecule.

The inclusion complex of the invention may be prepared from aqueous solutions, slurries or pastes of alprazolam and cyclodextrin according to conventional methods. The molar ratio of alprazolam to cyclodextrin may vary between 1:1 to 1:10 inclusive, but more preferably between 1:1 to 1:7 inclusive. Solutions are prepared by dissolving the cyclodextrin in a sufficient quantity of purified deionised water having a pH of 7. Alprazolam is added to the solution with stirring until dissolved. The dissolution of the alprazolam decreases the pH of the solution, but only from 7 to 6.4.

Figure 1:
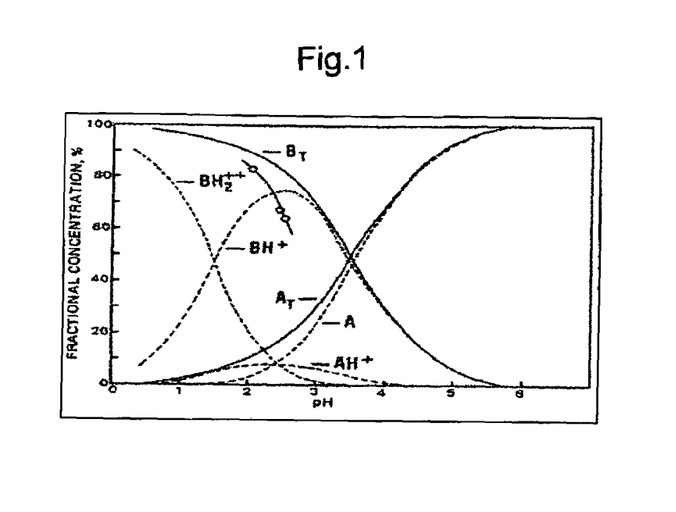
FIG. 1 shows the fractional concentration of various ionic species involved in the A⇌B reaction of alprazolam as a function of pH. (Cho, M. J., Scahill, T. A. and Hester, J. B. 1983. Kinetics and equalibrium of the reversible alprazolam ring-opening reaction. Journal of Pharmaceutical Science, 72).

Cyclic amines (including benzodiazepines) are known to undergo reversible pH-dependent ring-opening though formation of aldehyde or ketone and a primary amine (see FIG. 1). Under certain conditions, it is possible that both the open and closed forms may be present in solution, often resulting in an increased aqueous solubility of said drug. (Loftsson, T., Guðmundsdóttir, H., Sigurjónsdóttir, J. F., Sigurðsson, H. H., Sigfússon, S. D., Másson, M. and Stefánsson, E. 2001. Cyclodextrin solubilization of benzodiazepines: formulation of midazolam nasal spray. International Journal of Pharmaceutics, 212: 29–40.). In the case of certain benzodiazepines, and specifically alprazolam, the ring-open form is stable at certain pH values and can contribute to the overall drug aqueous solubility (Cho, M. J., Scahill, T. A. and Hester, J. B. 1983. Kinetics and equalibrium of the reversible alprazolam ring-opening reaction. Journal of Pharmaceutical Science, 72: 356–362). As may be seen in FIG. 1, it is clear that alprazolam (A) undergoes a 1,4-benzodiazepine ring-opening reaction in an acidic medium to form a benzophenone compound (B). The reaction between the ring-open and ring-closed forms is usually in equilibrium depending on the pH of the solution in which alprazolam is incorporated. The reaction is a reversible cyclization reaction, where both the ring-open and ring-closed forms exist in various ionic and non-ionic forms, due to mono- and di-protonation of the nitrogen in the 4-position in the azepine ring. An analysis of FIG. 1 shows that there is no ring-open alprazolam above pH 6. The reason for this may be attributed to the availability of the amount of protons present within the solvent to protonate the nitrogen in position 4 of the azepine ring, thus maintaining the drug in the ring-closed form (Loftsson et al., 2001 Cyclodextrin solubilisation of benzodiazepines: formulation of midazolam nasal spray. International Journal of Pharmaceutics, 212:29–40).

Figure 2:
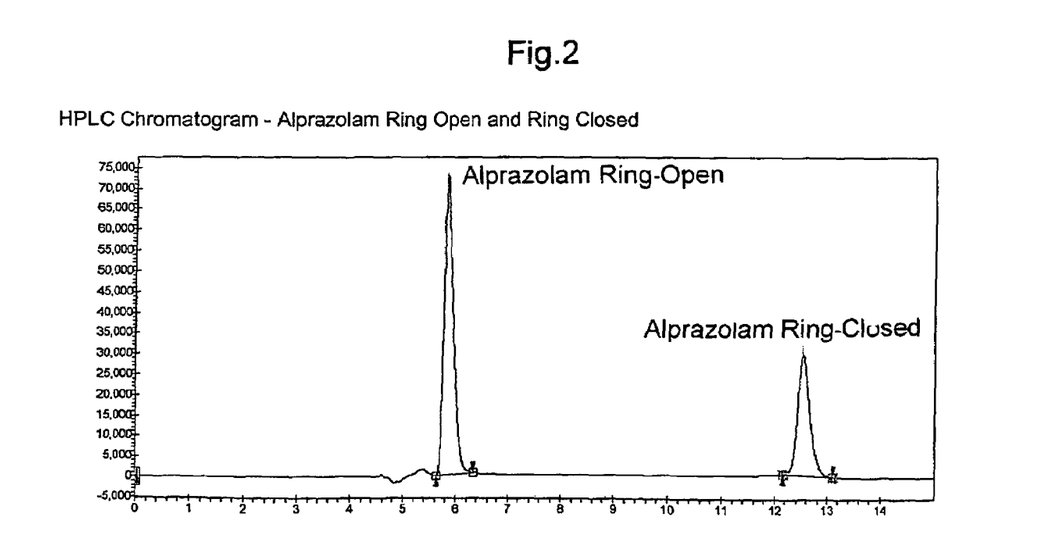
FIG. 2 is a HPLC chromatogram of alprazolam at pH 3, indicating the retention times of alprazolam in the ring-open form (6.3 minutes) and ring-closed form (13.1 minutes).

It is therefore clear that, in the solution of the present invention, which has a pH greater than 6, all the alprazolam is in ring-closed form. Further, FIG. 2, which is a chromatogram of alprazolam at pH 3 shows two primary peaks—one at 6.3 minutes and one at 13.1 minutes. The peak at 13.1 minutes represents alprazolam in the ring-closed form. The peak visible at 6.3 minutes is that of alprazolam in the ring-open form. The HPLC analysis shown in FIG. 3 of the sublingual formulation of Example 5 conducted according to the HPLC method used by Loftsson et. al. (2001 Cyclodextrin solubilization of benzodiazepines: formulation of midazolam nasal spray. International Journal of Pharmaceutics, 212: 29–40.) shows only one peak at 13 minutes (ring-closed alprazolam) and no peak at 6.3 minutes (ring-open alprazolam), thus indicating that all the alprazolam is present in ring-closed form.

A second advantage of the solution of the present invention is that the formulation is at a pH which will not result in mucosal irritation.

The solution may be used in the preparation of liquid delivery systems such as drops, sprays or aerosols. Where a solid inclusion complex is desired, the solution or slurry may be dried by spray drying or freeze drying.

Alternatively, alprazolam and cyclodextrin are mixed. The powder mixture is wetted with deionised water having a pH of 7 while mixing vigorously until a paste is formed. The paste has a pH of greater than 6, and all the alprazolam is in ring-closed form. The paste is mixed for 0.25 to 2 hours and dried in an oven or in vacuo at elevated temperature. The dried complex is crushed and sieved to the desired particle size.

When reconstituted with water having a pH of 7, the resulting solution has a pH of greater than 6, which means all of the alprazolam is in the ring-closed form. An advantage of this is that when a solid composition in the form of a sub-lingual tablet is used, all of the alprazolam, when dissolved in the mouth, is in the ring-closed form which increases the absorbtion of the drug across the mucosal membrane. The pH of saliva is between 6.5 and 7.5 (DeGrande, et al. 1996. Specialized oral mucosal drug delivery systems: Patches. In. Oral mucosal drug delivery, Marcel Dekker:New York, p. 286) and hence the alprazolam will remain in the ring-closed form. A second advantage is that the dissolved composition does not lower the pH of the patient's saliva to an extent that it causes oral mucosal irritation.

The particle size of the complex is preferably 95% less than 100 microns and most preferably 95% less than 50 microns, to facilitate wetting of a solid formulation.

The second aspect of the invention is a pharmaceutical composition which comprises as an active ingredient an inclusion complex, wherein all the alprazolam is in ring-closed form, as described above.

The pharmaceutical composition of the invention is of particular application in the treatment of GAD and for the management of panic disorders.

Further, the pharmaceutical composition of the invention is preferably adapted for oral, nasal, or rectal mucosal delivery.

The administration of an anxiolytic drug through the mucosal tissue of the nose, mouth or rectum avoids the problems associated with oral administration of alprazolam (i.e. slow onset of action, low bio-availability and associated poor compliance).

Absorption of the drug from the pharmaceutical composition of the invention is rapid such that the drug reaches the systemic circulation almost as fast as through injection and appreciably faster than oral administration, which is highly advantageous for the rapid relief of anxiety.

Further, the unpleasant taste and irritant properties of the active principle are reduced by presenting the drug to the nasal or rectal oral mucosal membranes in the form of a cyclodextrin inclusion complex.

The present invention achieves these advantages by molecular encapsulation of the drug in a cyclodextrin, so forming a molecular inclusion complex which may be used in the solid form for the preparation of sublingual or buccal tablets, buccal patches, nasal inhalation powders (insufflations), suppositories, or powder aerosols for nasal or pulmonary application. The inclusion complex may be used in the liquid state for the preparation of metered dose sprays, drops or pressurised aerosols for nasal or oral administration. The complex according to the invention may be incorporated into a shear form matrix designed for immediate release as described in Fuisz Technolgies Ltd. patents (Eur. Pat. Appl. EP 95-650038 and PCT Int. Appl. WO 95/34293).

The water soluble complexes of alprazolam according to the invention may be incorporated into controlled release matrices for sustained release following oral administration of a matrix tablet. The matrix may be composed of any suitable erodible matrix such as substituted celluloses and the like.

Alternatively the complexes may be applied to non-pareil spheres by coating methods known in the art. The coated spheres may be optionally coated with controlled release polymers such as polyacrylates and the like.

According to the invention, alprazolam has been found to be included in the cavity of 2-hydroxypropyl-beta-cyclodextrins to form molecular inclusion complexes. The inclusion complexes of alprazolam may therefore be prepared according to methods known in the art such as spray drying, freeze drying and kneading, as described above. The complexes according to the invention may also be incorporated into microspheres by methods appreciated in the art. The complexes according to the invention are stable and highly water soluble.

Penetration enhancers may be used to promote the passage of alprazolam across the mucosal membranes. Typical permeation enhancers include fatty acids and their salts such as sodium caprate, sodium caprylate and sodium oleate, sodium laurate, and bile salts such as sodium glycodeoxycholate, sodium glycocholate, sodium cholate and sodium laurodeoxycholate. Other penetration enhancers may include tensides, ionic surfactants such as sodium lauryl sulphate, or non-ionic surfactants such as polyethylene glycol 660 hydroxystearate or polyoxyethylene lauryl ethers, fusidates such as sodium taurodihydrofusidate. Other specific enhancers include azone and chitosan.

Combinations of permeation enhancers such as polyoxyethylene 8 lauryl ether and sodium glycocholate or mixed micelles such as sodium caprate and sodium glycocholate may also be used. The penetration enhancers may also be used in combination with sulfoalkyl derivatives. Typical concentrations of permeation enhancers are between 0.1% to 5%, more preferably between 0.25% to 3% by weight of the composition.

Liquid compositions suitable for nasal or oral administration may contain a suitable quantity of viscosity modifying agents such as hypromellose orcarbopol 934P and preservative agents such as benzalkonium chloride, chlorhexidine gluconate or thiomersal.

Oral compositions may contain suitable flavouring and sweetening agents such as cherry, mint, spearmint, vanilla, aspartame, sucrose, xylitol, saccharin and the like.

Typical sublingual or buccal tablets may include lubricants such as magnesium stearate, calcium stearate and sodium stearyl fumarate to facilitate tablet compression, diluents such as lactose, microcrystalline cellulose, maize starch and the like and mucoadhesive agents such as chitosan, carbopol 934P, and hydroxypropylcellulose and the like.

Typical disintegrants to enhance sublingual tablet disintegration may include sodium carboxymethylcellulose, sodium starch glycolate, polyplasdone XL, and dried starch.

Typical suppositories may be formulated according to methods known in the art described in the Pharmaceutical Codex 12''' Edition, the Pharmaceutical Press, pp 170–176 or Remington's Pharmaceutical Sciences 18th Edition, Mack Publishing Company, pp 1609–1614.

The following examples illustrate the present invention.

EXAMPLE 1

Figure 4:
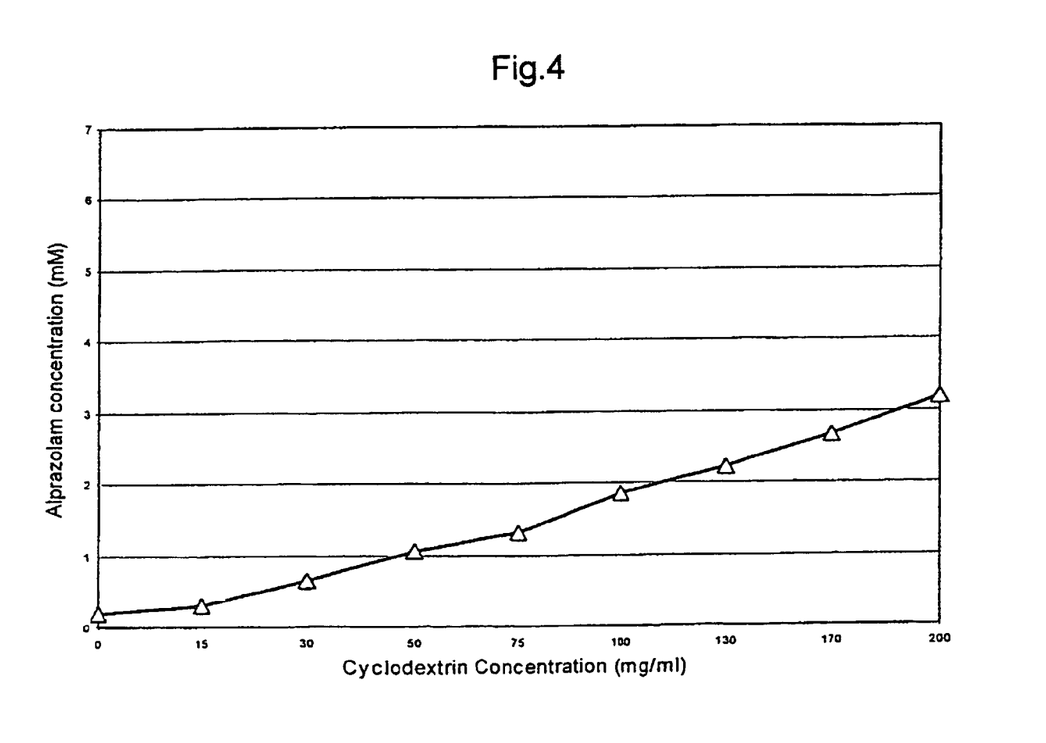
FIG. 4 represents the effect of 2-hydroxypropyl-beta-cyclodextrin on the aqueous solubility of alprazolam at 25° C.

An excess of alprazolam is added to aqueous solutions of varying concentrations of 2-hydroxypropyl-beta-cyclodextrin. The mixtures are shaken for 24 hours and filtered. The filtrate is analysed by Ultraviolet spectrophotometry for alprazolam concentration. The concentration of alprazolam is plotted as a function of cyclodextrin concentration in FIG. 4.

EXAMPLE 2

Alprazolam (6.53 g) and 2-hydroxypropyl-beta-cyclodextrin (200.4 g) are mixed. Purified deionised water (70 ml) with a pH of 7 is added with vigorous kneading to form a uniform paste with optional heating. The pH of the paste is 6.4. Kneading is continued for 5 hours and the paste is dried in vacuo at 80° C. The dried complex is crushed and passed through a 250 micron sieve.

EXAMPLE 3

Dissolution behaviour of the inclusion complex prepared in Example 2 and its corresponding physical mixtures was evaluated in phosphate buffer pH 6.8 using USP Apparatus I (basket, 100 rpm, 500 ml, 37° C.).

Figure 5:
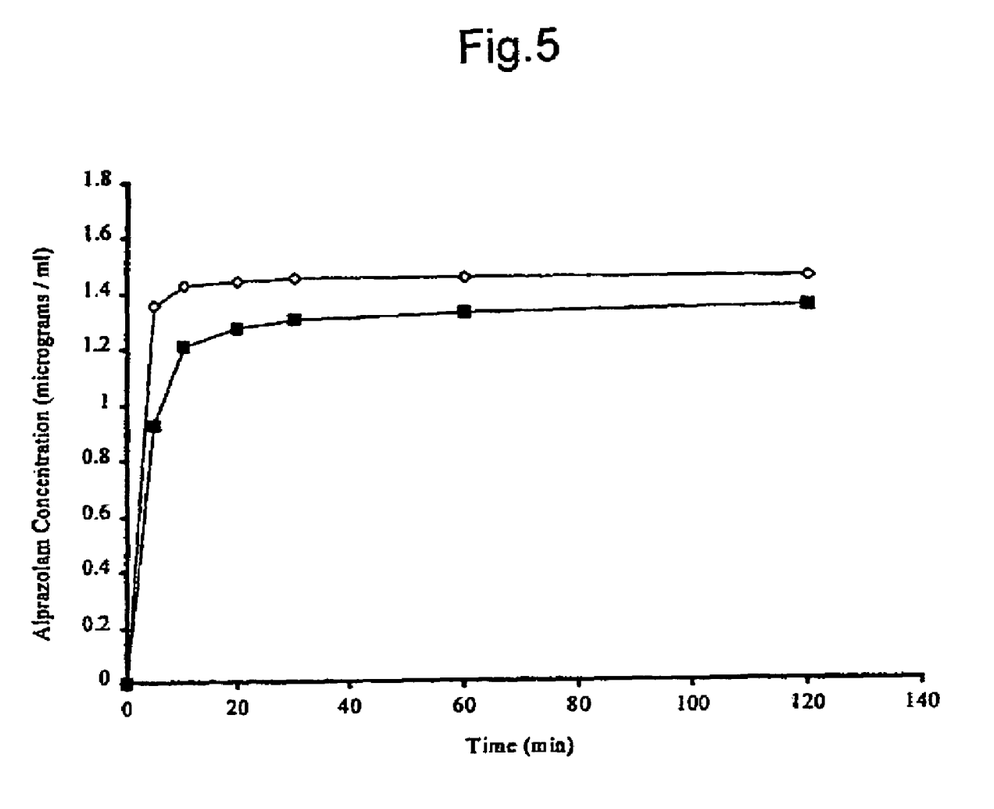
FIG. 5 represents the dissolution rate of alprazolam from a physical mixture (solid squares) of alprazolam and 2-hydroxypropyl-beta-cyclodextrin and the corresponding complex (open diamonds) obtained from Example 2 and performed according to Example 3.

Compressed disks (200 mg) containing an amount of inclusion complex or physical mixture equivalent to 1 mg alprazolam were prepared using a single punch and die. The dissolution rate of alprazolam from the system is shown in FIG. 5.

The complex of Example 2 results in a significantly faster dissolution rate within the first 20 minutes compared with the physical mixture.

EXAMPLE 4

The powdered inclusion complex prepared according to Example 2 was stored in an oven at 60° C. Chromatographic analysis showed the complex to be chemically stable after one months storage at 60° C.

EXAMPLE 5

A pre-mixture of alprazolam (3.87 g) and 2-hydroxypropyl-beta cyclodextrin (150 g) was prepared by geometric dilution in a mortar as follows:
1. Alprazolam 3.87 g+2-hydroxypropyl-beta cyclodextrin 3.78 g was mixed with a pestle for 3 minutes.
2. 2-hydroxypropyl-beta cyclodextrin 7.58 g was added to the mortar and mixed for 3 minutes.
3. 2-hydroxypropyl-beta cyclodextrin 15.12 g was added to the mortar and mixed for 5 minutes.
4. 2-hydroxypropyl-beta cyclodextrin 30.24 g was added to the mortar and mixed for 10 minutes.
5. The remaining 2-hydroxypropyl-beta cyclodextrin was added to the mortar and mixed for 20 minutes. The mixture was free of any lumps.

After complete mixing, the mixture was placed in a laboratory kneader and dry mixed for 10 minutes. 55 ml of boiling purified water with a pH of 7.0 was gradually added to the alprazolam-2-hydroxypropyl-beta cyclodextrin powder mixture to form a slurry. The pH of the slurry was measured and found to be 6.4. Kneading was commenced for 5 hours, after which the alprazolam-2-hydroxypropyl-beta cyclodextrin complex was dried by vacuum. Once dry, the alprazolam-2-hydroxypropyl-beta cyclodextrin complex was transferred to an airtight, light resistant container and sealed.

EXAMPLE 6

A pre-mixture of alprazolam (3.87 g) and 2-hydroxypropyl-beta cyclodextrin (150 g) was prepared by geometric dilution in a mortar as follows:
1. Alprazolam 3.87 g+2-hydroxypropyl-beta cyclodextrin 3.78 g was mixed with a pestle for 3 minutes.
2. 2-hydroxypropyl-beta cyclodextrin 7.58 g was added to the mortar and mixed for 3 minutes.
3. 2-hydroxypropyl-beta cyclodextrin 15.12 g was added to the mortar and mixed for 5 minutes.
4. 2-hydroxypropyl-beta cyclodextrin 30.24 g was added to the mortar and mixed for 10 minutes.
5. The remaining 2-hydroxypropyl-beta cyclodextrin was added to the mortar and mixed for 20 minutes. The mixture was free of any lumps.

After complete mixing, the mixture was placed in a laboratory kneader and dry mixed for 10 minutes. 55 ml of boiling purified water with a pH of 7.0 was gradually added to the alprazolam-2-hydroxypropyl-beta cyclodextrin powder mixture to form a slurry. The pH of the slurry was measured and found to be 6.4. The pH of the slurry was adjusted to 7.0 with a 10 mM NaOH solution. Kneading was commenced for 5 hours, after which the alprazolam-2-hydroxypropyl-beta cyclodextrin complex was dried by vacuum. Once dry, the alprazolam-2-hydroxypropyl-beta cyclodextrin complex was transferred to an airtight, light resistant container and sealed.

EXAMPLE 7

Figure 3:
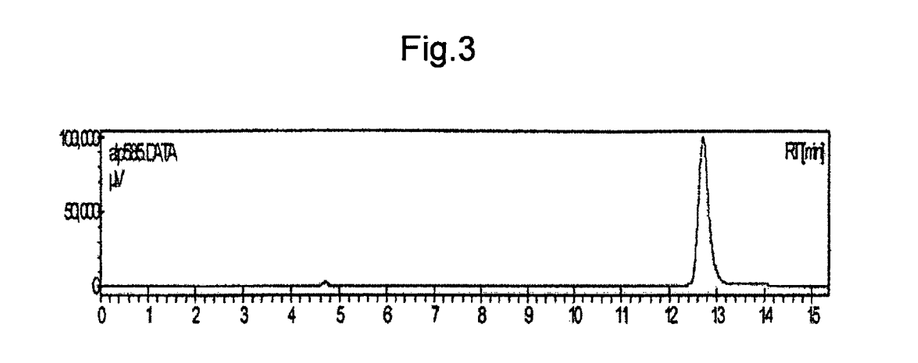
FIG. 3 is a HPLC analysis of alprazolam-cyclodextrin complex as prepared by the method of the invention.

The reconstitution of the solid inclusion complex of alprazolam-2-hydroxypropyl-beta-cyclodextrin (Example 5) with deionised water with a pH of 7 resulted in an alprazolam-2-hydroxypropyl-beta-cyclodextrin solution with a pH of 6.4, with all of the alprazolam in the ring-closed form (FIG. 3).

EXAMPLE 8

The unit composition of a 50 mg sublingual tablet containing the equivalent of 0.5 mg alprazolam was as follows:

| | |
|---|---|
| Lactose NF | 16.0 mg |
| Sodium stearyl fumarate | 0.7 mg |
| Microcrystalline cellulose PH200 | 4.1 mg |
| Ac-di-sol | 1.4 mg |
| Purified talc | 2.1 mg |
| Sweatner | 4.0 mg |
| Mint flavour | 1.4 mg |
| Alprazolam/2-hydroxypropyl-beta cyclodextrin complex (Example 6) | 20.3 mg |
| Total mass per tablet | 50.0 mg |

EXAMPLE 10

The unit composition of a 100 mg sublingual tablet containing the equivalent of 1.0 mg alprazolam was as follows:

| | |
|---|---|
| Lactose NF | 8.5 mg |
| Magnesium stearate | 0.5 mg |
| Microcrystalline cellulose PH200 | 43.6 mg |
| Ac-di-sol | 2.3 mg |
| Purified talc | 0.8 mg |
| Sweatner | 0.6 mg |
| Mint flavour | 3.0 mg |
| Alprazolam/2-hydroxypropyl-beta cyclodextrin complex (Example 6) | 40.7 mg |
| Total mass per tablet | 100.0 mg |

EXAMPLE 11

The unit composition of a 100 mg oral tablet containing the equivalent of 0.5 mg alprazolam was as follows

| | |
|---|---|
| Avicel 200 | 71.5 mg |
| Magnesium stearate | 1.0 mg |
| Ac-di-sol | 5.0 mg |
| Opadry OYB 32908 | 2.2 mg |
| Alprazolam/2-hydroxypropyl-beta cyclodextrin complex (Example 6) | 20.3 mg |
| Total mass per tablet | 100.0 mg |

EXAMPLE 12

The unit composition of a 100 mg oral tablet containing the equivalent of 1.0 mg alprazolam was as follows

| | |
|---|---|
| Avicel 200 | 51.1 mg |
| Magnesium stearate | 1.0 mg |
| Ac-di-sol | 5.0 mg |
| Opadry OYB 32908 | 2.2 mg |
| Alprazolam/2-hydroxypropyl-beta cyclodextrin complex (Example 6) | 40.7 mg |
| Total mass per tablet | 100.0 mg. |

The invention claimed is:

1. A pharmaceutical composition for transmucosal delivery comprising an inclusion complex of (a) alprazolam and (b) a water soluble 2-hydroxypropyl-beta-cyclodextrin, and a pharmaceutically acceptable carrier therefor, wherein all the alprazolam is present in ring-closed form.

2. A pharmaceutical composition according to claim 1, when in liquid form having a pH greater than 6, and when in solid form having a pH of greater than 6 when reconstituted with water having a pH of 7.

3. A pharmaceutical composition according to claim 1, wherein the 2-hydroxypropyl-beta-cyclodextrin has a degree of substitution between 3.9 and 5.1 hydroxypropyl groups per cyclodextrin molecule.

4. A pharmaceutical composition according to claim 1, wherein the inclusion complex has a stoichiometry of (a) to (b) of from 1:1 mol/mol to 1:10 mol/mol inclusive.

5. A pharmaceutical composition according to claim 4, wherein the inclusion complex has a stoichiometry of (a) to (b) of from 1:1 mol/mol to 1:7 mol/mol inclusive.

6. A pharmaceutical composition according to claim 1, wherein the pharmaceutical composition comprises a solution of the inclusion complex of alprazolam and the cyclodextrin in a pharmaceutical acceptable liquid carrier.

7. A pharmaceutical composition according to claim 6, formulated for administration as drops, a spray or an aerosol.

8. A pharmaceutical composition according to claim 1, wherein the inclusion complex of alprazolam and the 2-hydroxypropyl-beta-cyclodextrin is a solid mixed with or incorporated into a pharmaceutical acceptable solid carrier.

9. A pharmaceutical composition according to claim 8 formulated as oral tablets, sublingual tablets, buccal tablets, buccal patches, nasal inhalation powders, suppositories, and powder aerosols.

10. An inclusion complex of alprazolam and a water soluble 2-hydroxypropyl-beta-cyclodextrin, wherein all the alprazolam is in ring-closed form.

11. The inclusion complex according to claim 10, when in liquid form, having a pH of greater than 6, and when in solid form having a pH of greater than 6 when reconstituted with water having a pH of 7.

12. The inclusion complex according to claim 10, wherein the 2-hydroxypropyl-beta-cyclodextrin has a degree of substitution between 3.9 and 5.1 hydroxypropyl groups per cyclodextrin molecule.

13. The inclusion complex according to claim 10, wherein the inclusion complex has a stoichiometry of (a) to (b) of from 1:1 mol/mol to 1:10 mol/mol inclusive.

14. The inclusion complex according to claim 13, wherein the inclusion complex has a stoichiometry of (a) to (b) of from 1:1 mol/mol to 1:7 mol/mol inclusive.

* * * * *